(12) United States Patent
Brockett et al.

(10) Patent No.: US 12,622,748 B2
(45) Date of Patent: May 12, 2026

(54) APPARATUS FOR APPLICATION OF EVANESCENT WAVES TO BIOLOGICAL TISSUES

(71) Applicant: EVANESC THERAPEUTICS, INC., Encino, CA (US)

(72) Inventors: Timothy J. Brockett, Malibu, CA (US); Mehran Matloubian, Encino, CA (US); Gregg A. Hollingsworth, Tempe, AZ (US)

(73) Assignee: EVANESC THERAPEUTICS, INC., Encino, CA (US)

( * ) Notice: Subject to any disclaimer, the term of this patent is extended or adjusted under 35 U.S.C. 154(b) by 511 days.

(21) Appl. No.: 18/179,247

(22) Filed: Mar. 6, 2023

(65) Prior Publication Data

US 2023/0200904 A1 Jun. 29, 2023

Related U.S. Application Data

(63) Continuation-in-part of application No. 17/539,968, filed on Dec. 1, 2021, now Pat. No. 11,911,098, and (Continued)

(51) Int. Cl.
*A61B 18/18* (2006.01)
*A61B 18/00* (2006.01)

(52) U.S. Cl.
CPC .... *A61B 18/18* (2013.01); *A61B 2018/00446* (2013.01); *A61B 2018/00797* (2013.01)

(58) Field of Classification Search
CPC ......... A61B 18/18; A61B 2018/00446; A61B 2018/00797; A61N 1/36002; A61N 1/40; A61N 2/02; A61N 5/00
See application file for complete search history.

(56) References Cited

U.S. PATENT DOCUMENTS

| | | | |
|---|---|---|---|
| 4,822,470 A | 4/1989 | Chang | |
| 4,846,178 A | 7/1989 | Fuxue et al. | |

(Continued)

FOREIGN PATENT DOCUMENTS

| | | | |
|---|---|---|---|
| CN | 104703536 A | 6/2015 | |
| CN | 106267592 A | 1/2017 | |

(Continued)

OTHER PUBLICATIONS

International Search Report and Written Opinion for related application PCT/US2021/053628, mailed Jan. 26, 2022.

(Continued)

*Primary Examiner* — Michael F Peffley
(74) *Attorney, Agent, or Firm* — Ogawa P.C.

(57) ABSTRACT

There are many devices that are used to deliver electromagnetic energy to biological tissues. However, physical properties of current techniques limit the strength and efficacy of the applied field. This invention introduces a new apparatus for the application of evanescent waves into biological tissue. The apparatus is planar, conformal, and electrically insulated and is comprised of two or more conductive regions spatially separated by a non-conductive gap insulated by low-dielectric constant, non-conductive material. The apparatus is powered by one or more RF voltage sources that can be applied to individual or several conductive regions to create voltage differentials that generate evanescent waves. The apparatus can be used for treating cancer tumors, deep brain stimulation, and other therapeutic purposes.

27 Claims, 15 Drawing Sheets

Related U.S. Application Data a continuation-in-part of application No. 17/080,708, filed on Oct. 26, 2020, now abandoned, said application No. 17/539,968 is a continuation of application No. 16/183,427, filed on Nov. 7, 2018, now Pat. No. 11,213,349.

(60) Provisional application No. 62/582,788, filed on Nov. 7, 2017.

(56) References Cited

U.S. PATENT DOCUMENTS

| | | | | |
|---|---|---|---|---|
| 5,186,181 | A | * | 2/1993 | Franconi ................. A61N 5/02 607/46 |
| 5,540,681 | A | | 7/1996 | Strul et al. |
| 6,813,515 | B2 | | 11/2004 | Hashimshony |
| 6,868,289 | B2 | * | 3/2005 | Palti ......................... A61N 1/40 607/76 |
| 7,599,746 | B2 | | 10/2009 | Palti |
| 7,805,201 | B2 | * | 9/2010 | Palti ......................... A61N 1/40 607/76 |
| 8,641,704 | B2 | | 2/2014 | Werneth et al. |
| 8,706,261 | B2 | | 4/2014 | Palti |
| 8,715,203 | B2 | | 5/2014 | Palti |
| 8,911,342 | B2 | | 12/2014 | Dissing et al. |
| 9,433,797 | B2 | | 9/2016 | Pilla et al. |
| 10,046,172 | B2 | | 8/2018 | Butters et al. |
| 2005/0107718 | A1 | | 5/2005 | Hashimshony |
| 2009/0076366 | A1 | | 3/2009 | Palti |
| 2010/0324547 | A1 | | 12/2010 | Palti |
| 2013/0267946 | A1 | | 10/2013 | Brannan et al. |
| 2015/0374471 | A1 | | 12/2015 | Stangel |
| 2016/0303386 | A1 | | 10/2016 | Poon et al. |
| 2017/0259071 | A1 | | 9/2017 | Poon et al. |
| 2018/0085593 | A1 | | 3/2018 | Fayram et al. |
| 2019/0133683 | A1 | | 5/2019 | Matloubian et al. |

FOREIGN PATENT DOCUMENTS

| | | | |
|---|---|---|---|
| CN | 106659901 | A | 5/2017 |
| CN | 106999721 | A | 8/2017 |
| CN | 108472071 | A | 8/2018 |
| KR | 10-2015-0049679 | A | 8/2015 |
| WO | 2015179225 | A1 | 11/2015 |

OTHER PUBLICATIONS

International Search Report and Written Opinion for PCT/US18/59663 mailed Jan. 11, 2019.

India Office Action for related application 202027015304, mailed Mar. 9, 2022.

B.E Lyons et al., "Localized Hyperthermia in the Treatment of Malignant Brain Tumors Using an Interstitial Microwave Antenna Array," IEEE Transactions on Biomedical Engineering, vol. BME-31, Issue :1, Jan. 1984.

Examination Report for related German Application No. 11 2018 005 767.4, mailed Jun. 8, 2022.

* cited by examiner

101

105

104

106

103

107

102

PRIOR ART

PRIOR ART

PRIOR ART

PRIOR ART

APPARATUS FOR APPLICATION OF EVANESCENT WAVES TO BIOLOGICAL TISSUES

CROSS-REFERENCES TO RELATED APPLICATIONS

This application is a continuation in part and claims priority to U.S. Ser. No. 17/080,708 filed Oct. 26, 2020, and is a continuation in part and claims priority to U.S. Ser. No. 17/539,968 filed Dec. 1, 2021, which is a continuation of U.S. Ser. No. 16/183,427 filed Nov. 7, 2018 (now U.S. Pat. No. 11,213,349 B2), which claims priority to U.S. Provisional Patent Application No. 62/582,788, filed Nov. 7, 2017, each of which is commonly assigned is hereby incorporated by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Electromagnetic fields have shown to cause biological response in many types of tissues and its application is common in many therapeutic, medical, and scientific procedures. Applications of these fields are accomplished with many different devices such as electrodes, coils, capacitive plates, among others. Each of these devices are typically powered by a connected or wireless source, where voltage, current, and/or electromagnetic waves are produced then coupled to the device and subsequently the tissue.

Common devices used to couple electromagnetic energy into tissues include electrodes, helical coils or spirals, capacitive plates, and antennas such as waveguides, horns, monopoles/dipoles, etc. Usually employed for diagnostics and monitoring, these devices are becoming more common in treatment of both acute and chronic diseases and conditions, such as solid tumor cancer treatment (U.S. Pat. Nos. 4,822,470 and 7,599,746 B2), depression and neurodegenerative conditions (U.S. Pat. Nos. 8,911,342 B2; and 9,433, 797 B2), and other ailments.

The most widely used devices are direct electrodes. Electrodes are conductive pads that, in conjunction with conductive gel, create a direct ohmic contact with the skin. They are typically connected to their electrical source by wires. When powered by a voltage source and a complete electric circuit is closed, electrical current passes directly through the tissues traveling from one electrode to the others, depending on the wiring configuration. Consequently, the voltage applied to the electrodes needs to be limited, as there is a risk of damaging the tissue due to high electrical currents or electrical disruption of biological processes such as in the heart or brain.

Coil devices, including helical coils, spirals, and loops are often deployed in diagnostic tools such as MRIs, wireless charging systems for medical devices such as pacemakers, and some treatment/therapeutic devices such as seen in U.S.

2

Pat. No. 10,046,172 B2. To operate these devices, a current is driven through the coil which produces a magnetic field that will penetrate any tissue within the coil. Any electrical response of the tissue by this field is induced within the tissue based on the electrical and magnetic properties of the tissue. Often, high current in the coil (and its resultant strong magnetic field) is required to observe a response in the tissue, requiring large coils, expensive magnetics, and powerful electrical sources.

Capacitive plates operate like electrodes, however, in general they are placed directly across from one another with the tissue in between. In addition, capacitive plates are insulated from the skin by non-conductive material such as plastic, silicone, or ceramic. Capacitive plates are primarily used to create an electric field within the tissue, whose strength is determined by voltage differential applied to the plates, the distance between the capacitive plates, the dielectric properties of the insulating layer, and the dielectric properties of the tissue. In some designs of capacitive plates, it is possible to induce large amounts of electrical current, which can damage the tissue in a similar manner to the direct electrodes. As with the electrodes, this can limit the voltage level that can be applied to the plates, reducing the maximum strength of the electric field and likely reducing the efficacy of the treatment or measurement.

Other devices to couple electromagnetic energy include waveguides (U.S. Pat. No. 6,813,515 B2), antennas, and coupled wires (U.S. Pat. No. 4,822,470). In typical waveguides and antennas, a resonant structure is used to propagate traveling electromagnetic waves to be incident on the tissue, where, depending on the tissue's dielectric properties, energy is absorbed. In this case, the waveguide and antennas are usually separated by a significant gap or insulator.

In many cases of applying electromagnetic fields to biological tissue, it is imperative to be able to control the locality, strength, and direction/polarization of the fields. An example is in cancer tumor treatment (U.S. Pat. No. 7,805, 201 B2), where a localized tumor must be illuminated with a certain strength of electromagnetic energy and periodically be exposed to two or more polarizations of the electromagnetic field. Each of the devices used to apply electromagnetic fields have distinct disadvantages when trying to achieve this type of control.

Firstly, electrodes, coil devices, capacitive plates, and insulated wires are difficult to localize within the tissue. Electrodes and capacitive plates, for example, often have their respective high and low voltage potential elements relatively far apart. This allows the electromagnetic fields to spread throughout the tissue, usually spreading through tissues that are not the target of the fields. This increases power dissipation and possibly increases side effects. Similarly, coils are often required to surround the tissue being illuminated, spreading magnetic fields throughout the entirety of the tissue with increased power dissipation and potential side effects. Resonant antennas and waveguides are usually unbounded devices, with the area that electromagnetic fields illuminate significantly dependent on the overall aperture size of the device: The larger the dimensions of the aperture, the less area and more targeted the electromagnetic fields are directed. Targeted treatment, with local application of fields, often becomes impractical since it requires the device to be very large in size and cumbersome to handle or attach to tissues.

The devices described above also have difficultly in dynamically changing polarization of the fields. In general, each device above can only apply one polarization unless subsequent extra devices are included. For example, to change polarizations for electrodes, a third electrode and a switch (or second voltage source) is required. By changing the circuit path of the three-electrode system, one can redirect the direction of the fields between the three electrodes. To achieve a significant angle difference between the different polarizations, it often requires the three electrodes to be placed relatively far from the second electrode. Both capacitive plates and coils have similar limitations. The one exception is an antenna, since it is possible to create dual-polarization antennas that can apply two (or more) polarizations from the same device depending on how the antenna is powered.

Finally, a distinct disadvantage that resonant antennas and single conductor waveguides exhibit are limited frequency bandwidth. Often, this limitation requires the need for additional devices to be available if it is required to change the electromagnetic signal's frequency for any reason. Clearly, there is room for improved devices and apparatuses that can address the disadvantages of current devices.

BRIEF SUMMARY OF THE INVENTION

In this invention a novel apparatus to couple electromagnetic energy efficiently and dynamically into biological tissues is described. The apparatus comprises of a singular, conformal planar, and insulated antenna system with the ability to excite and deliver localized evanescent waves into adjacent tissue. In addition, its arrangement can allow for dynamic control of field strength and polarization without additional apparatuses, simplifying the overall system and reducing the overall size and improving the convenience of the apparatus.

The apparatus can be described as an arrangement of planar and conformal conductive regions separated by non-conductive gaps and powered by one or more AC/RF voltage sources or amplifiers. The configuration of the conductive and non-conductive gaps depends on the electric field strength and polarization desired. Furthermore, the apparatus is substantially insulated with non-conductive, low-dielectric constant material to primarily allow tangential electric fields to be incident on the biological tissue and substantially block normal electric fields. This configuration allows for the apparatus to operate in an impedance regime that mimics a parallel circuit. This differs from other devices such as electrodes and capacitive plates which operate in an impedance regime that mimics a series circuit.

An example of an arrangement of conductive and non-conductive regions can be, but not limited to, a conductive rectangular disk region 15 cm by 12 cm surrounded by a conductive concentric rectangular ring 1 cm in width separated by non-conductive gap of 1 cm. The entire apparatus would be insulated with a low dielectric constant material such as polyimide at least 25 microns thick. Each conductive region would be wired to one or more AC/RF voltage sources or amplifiers where a voltage differential is imposed across the non-conductive gap. The resultant evanescent waves and reactive fields would emanate from the apparatus where it can be coupled to any adjacent material or tissue.

Distinct advantages emerge with this apparatus, especially in terms of treatment of solid tumor cancers and other localized ailments: Firstly, the apparatus allows for targeted and localized application of electromagnetic fields, reducing dissipated power and potential side-effects. Secondly, the apparatus is inherently broadband, allowing for delivery of a wide range of electromagnetic waves over a large frequency range without the need for additional apparatuses. Thirdly, the arrangement of the conductive and non-conductive regions and the inclusion of multiple voltage sources or amplifiers allows for dynamic control of field strength and polarization, allowing for multiple field configurations for varied and periodic application of the waves. Finally, the planar and conformal design of the apparatus allows for easy application and attachment to many different shapes and sizes of biological tissue and body parts.

Medical or biological applications that this apparatus can be used for can include, but not limited to, solid tumor cancer treatment, electric field therapy for depression, drug sensitizer, blood-brain barrier suppressor, and/or diagnostics.

BRIEF DESCRIPTION OF THE DRAWINGS

FIG. 7 is a drawing of yet another physical embodiment of the apparatus designed for the top of a human head or other part of the body.

DETAILED DESCRIPTION OF THE INVENTION

Figure 1A:
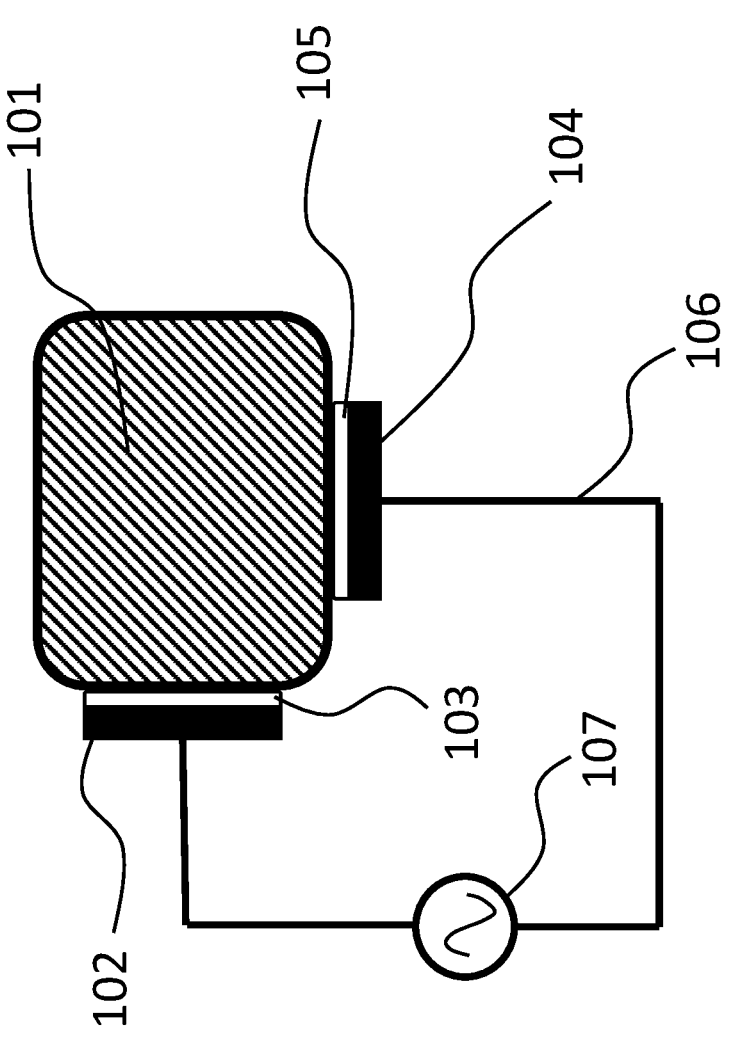
FIG. 1A is a drawing of an example of an electrode system to couple electric field and current to biological tissue.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details.

Please note, if used, the labels left, right, front, back, top, bottom, forward, reverse, clockwise and counter-clockwise have been used for convenience purposes only and are not intended to imply any particular fixed direction. Instead, they are used to reflect relative locations and/or directions between various portions of an object. Additionally, the terms "first" and "second" or other like descriptors do not necessarily imply an order but should be interpreted using ordinary meaning.

The invention describe here is an apparatus designed to emit and couple electromagnetic evanescent waves into biological tissues. The apparatus is a singular planar and conformal device comprised of conductive regions separated by non-conductive regions and gaps insulated by low-dielectric constant non-conductive materials. The conductive regions of the apparatus are individually connected to a single or multiple AC/RF voltage sources or amplifiers, of which are controlled to create at least one or more voltage differentials between adjacent conductive regions. The voltage differential produces and emits evanescent waves and supports reactive fields in the volume above and below the planar surface of the apparatus. When the apparatus is placed in the vicinity of biological tissue the evanescent waves penetrate and couple into the tissue.

The conductive regions of the apparatus are designed to be planar and made of electrically conductive material such as, but not limited to, copper, aluminum, brass, etc. To allow for conformal application to various tissue geometries, the conductive material should be thin and not rigid. It is required to have at least 2 or more electrically conductive regions. These regions, however, have no required shape or size, but should be designed to properly fit the tissue it is being applied to. The arrangement of these regions is also not required to be fixed; however, it is advantageous to arrange the regions within the desired aperture and be separated by a relatively small gap of around 1 cm. This is to ensure that the apparatus generates an electric field strong enough to couple to materials at a voltage differential that is practical. An example of a typical arrangement that the conductive regions could be, but are not limited to, a circular central conductive region 8 cm in diameter surrounded by a ring-like conductive region that is concentric and separated from the central conductive region by a 1 cm gap.

The conductive regions (and the accompanying gaps that separate them) should be insulated by non-conductive, low-dielectric constant material. Materials could be, but are not limited to, polyimide, plastic, polypropylene, Teflon, etc. The dielectric constant of the insulation should be less than 50. The purpose of the insulation is to first protect the tissue from electric shock and second to partially block the normal vector component of the electric field. The latter is necessary as it is important to ensure that the electromagnetic wave is subjected to an impedance regime that mimics a parallel circuit. This is achieved by primarily allowing the tangential vector component while minimizing the normal vector component that is incident upon the tissue. Operating in a parallel impedance regime is advantageous because it allows for increases in the electric field strength while limiting the overall power dissipation as compared to an electromagnetic wave subject to an impedance regime that mimics a series circuit. In addition, partially blocking the normal vector component of the electric field reduces the electric current draw in top layers of the tissue, which prevents heating and discomfort to the patient.

For effective coupling to tissues, the dimensions of the total aperture of the apparatus should be approximately the same size or slightly larger than the area of the tissue that should be exposed to the electromagnetic fields. In general, the evanescent waves will not significantly extend laterally beyond the outside edge of the apparatus and any tissue outside the aperture will not be illuminated significantly.

The apparatus is powered by AC/RF voltage sources and/or amplifiers connected to the conductive regions. In a simple embodiment, one rectangular conductive region is surrounded by a conductive region concentric regular ring with a gap of 1 cm separating the two regions. One AC/RF voltage source/amplifier has its positive terminal attached to the central conductive region with its negative terminal attached to the outside conductive ring region. This wiring arrangement creates a voltage differential between the two conductive regions which launches evanescent waves within the aperture of the ring's conductive region. When powered in this manner, the apparatus can be considered to act as a "wave-launcher" or evanescent-wave antenna. In another embodiment, the same apparatus has one AC/RF voltage source/amplifier's positive terminal attached to the central conductive region. A second AC/RF voltage source/amplifier has its positive terminal attached to the concentric ring region. The negative terminal of both voltage sources/amplifiers are then connected to one another. Finally, the phase of the first and second voltage sources/amplifiers are set to be 180 degrees out-of-phase. This wiring arrangement create a voltage differential that is the sum of the voltage level of both sources/amplifiers providing an evanescent wave with higher electric field strength than one source could do by itself.

As described, evanescent waves will be launched above and below the planar aperture of the apparatus. The polarization of the electric field that is associated with this evanescent wave is determined by the arrangement, shape, and direction of the conductive regions where voltage differential is present. For example, for the simple embodiment of a conductive circular disk surrounded by a conductive concentric circular ring separated by a non-conductive gap, the electric field polarization would extend radially from the center when a voltage differential is placed between the two conductors. If the apparatus includes three conductors, it is possible to actuate the electric field polarization by arranging the conductors to be at angles of each other and applying the voltage differential between the three conductors to change the angle of the polarization. Such physical arrangements and electronic configurations within a single apparatus allows for local application of waves without the need for a second or third apparatus to achieve dynamic control of polarization.

A specific application of this apparatus involves the treatment of solid tumor cancers in tissues. Based on one postulated mechanism of action, electric fields interfere with the dividing cancer cells during mitosis causing the cancer cells to die and the tumor to shrink. The electric fields do not impact non-dividing cells so there is no harmful impact to the non-dividing healthy cells. Effectiveness of the electric fields in disrupting the division of the cancer cells depends on several factors including the frequency of the RF source, the magnitude of the electric fields, and on the relative orientation (or polarization) of the electric fields and the axis of the dividing cells.

Different types of cancer cells respond to different frequencies of the RF source. For example, it has been demonstrated that for a number of glioblastoma cancer cells, a frequency of around 200 KHz is the optimum frequency to kill the cells while for lung cancer cells the optimum frequency has been demonstrated to be around 150 KHz.

In addition, the conductivity of the tumor also has an impact with a higher conductivity tumor leading to higher RF power densities in the tumor. A minimum RF power density of around 1 mW/cm³ is desired in the tumor; however, higher electric fields and higher RF power densities in the tumor will result in higher efficacy in killing cancer cells. The power density in the tumor is proportional to the square of the electric field in the tumor and is directly proportional to the conductivity of the tumor. So doubling the electric field in a tumor will increase RF power density in the tumor by a factor of four and a tumor with double the conductivity will have double the RF power density in the tumor.

In addition to the magnitude of the electric field, the effectiveness of killing cancer cells also depends on the orientation (polarization) of the electric field relative to the axis of dividing cells. In order to target more dividing cancer cells during treatment by capacitive coupling, two sets of electrodes are typically used to capacitively couple the electric fields in two different polarizations (typically the two polarizations are perpendicular to each other).

Based on other postulated mechanisms of action, exposure of the tumor cancer cells to RF fields can induce other responses that can damage or eliminate cells. For example, it is postulated that RF fields trigger an immunogenic response from the body, possibly by damaging tumor cells that alert the immune system to destroy them. Other responses may be related to reducing the formation of blood vessels to the tumor, slowing its growth and development, or, increases in the uptake by the cancer cells of cancer drugs being used in conjunction with the RF treatment, possibly by manipulating the pores on the surface of the tumor cells allowing easier passage of molecules into the cell.

The following is a detailed explanation of the figures:

FIG. 1A is a diagram of a typical pair of electrodes used to deliver or sense electrical signals from biological tissues. A first conductive electrode 102 is incident upon the biological tissue 101 with a conductive gel 103 filling the gap in between. Elsewhere on the surface of the biological tissue 101 is a second conductive electrode 104 with conductive gel 105 filling the gap between the electrode and surface of the tissue. The two electrodes are connected in a circuit with an AC voltage source 107 by wires 106. The voltage source actuates current within the circuit and tissue according to Ohm's law and allows electrical signals to travel through the tissue. This is the most common way to deliver electromagnetic energy to tissues.

Figure 1B:
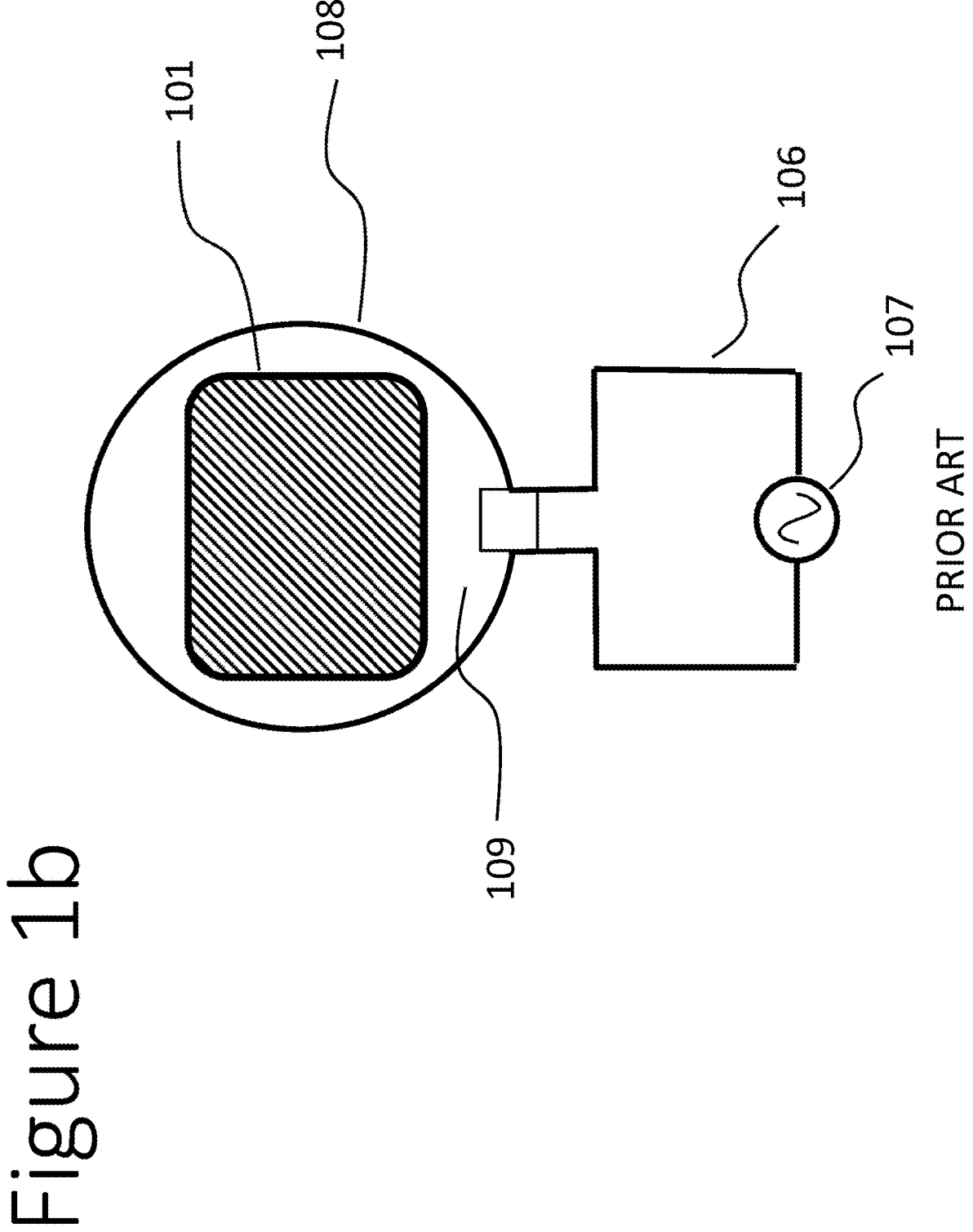
FIG. 1B is a drawing of an example of a loop system to couple electric field and current to biological tissue.

FIG. 1B is a diagram of an inductive loop system that can couple to a sample of biological tissue. The biological tissue 101 is surround by a loop 109 (or several loops) of wire 108. The loop is attached to an AC voltage source 107 by wire 106. Current is driven inside the loop that produces an electromagnetic field within the loop. The field then couples inductively inside the tissue. This is also a common way to deliver electromagnetic energy to tissues and is common in MRI.

Figure 1C:
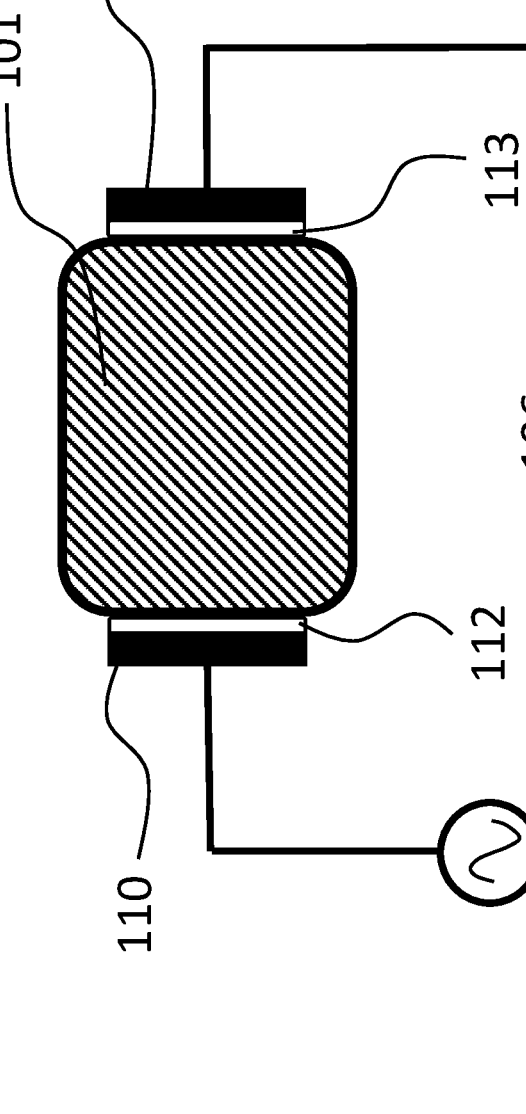
FIG. 1C is a drawing of an example of a capacitive system to couple electric field and current to biological tissue.

FIG. 1C is a diagram of a capacitive system that can couple to a sample of biological tissue. The biological tissue 101 is sandwiched between electrode 110 and electrode 111. Non-conductive insulation 112 and 113 separate the electrodes from the tissue to prevent direct current from passing through the tissue. The electrodes are connected into a circuit using wire 106 with an AC voltage source 107. When powered, an electric field is created between the electrodes, the strength determined by the distance between the electrodes, the size and dimensions of the insulating layers and electrodes, and the dielectric properties of the insulating layers and biological tissue. This technique of delivering electromagnetic fields into tissues have been used in cancer treatment and other applications.

Figure 1D:
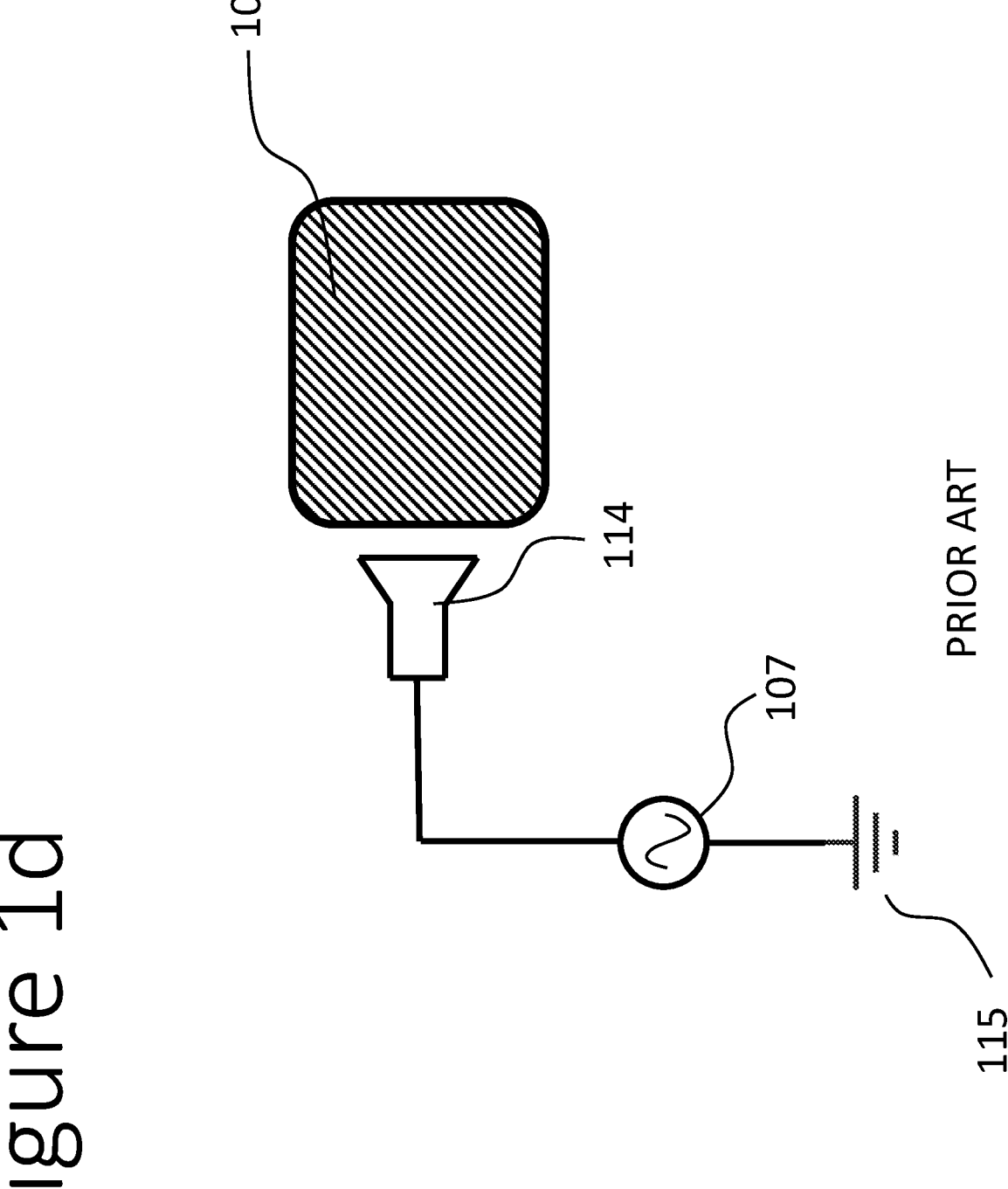
FIG. 1D is a drawing of an example of a narrow-band (waveguide) antenna system to couple electromagnetic fields to biological tissue.

FIG. 1D is a diagram of an antenna system that can couple electromagnetic energy into a sample of biological tissue. An antenna 114 is pointed and placed towards a sample of biological tissue 101. The antenna is attached to an AC voltage source 107 with one of its ports grounded 115. The voltage source actuates the antenna 114 and the antenna radiates in the direction of the biological tissue 101. Depending on the dielectric and magnetic properties of the biological tissue a portion or all of the radiative electromagnetic energy couples into the biological tissue.

Figure 2:
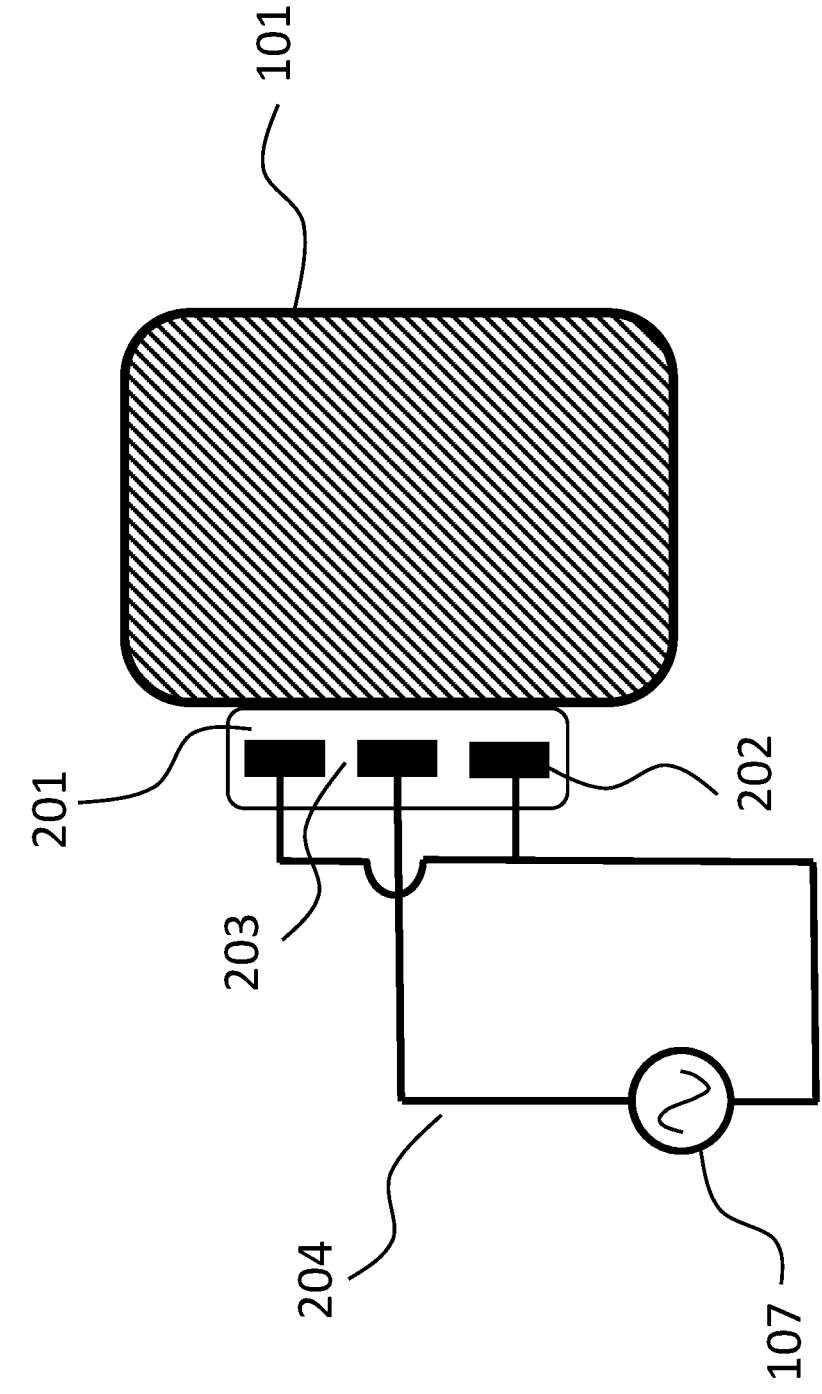
FIG. 2 is a drawing of a simple embodiment of a planar and conformal apparatus that can produce and couple evanescent waves into biological tissue.

FIG. 2 is a general diagram of the invention. Two or more conductive regions 202 are spatially placed in the vicinity of the surface of biological tissue 101 with non-conductive gaps 203 separating the conductive regions. The conductive regions 202 are substantially surrounded by low dielectric constant material 201 to insulate the biological tissue 101 from direct current and substantially block the normal component of the electric field. The conductive regions 202 are connected to an AC/RF voltage source 107 through wiring 204. With the proper wiring, the voltage source 107 applies a voltage differential between two or more of the conductive regions 202. The voltage differential produces evanescent wave that extend from the gaps 203 between the conductive regions 202 that penetrates and couples to the biological tissue 101.

Figure 3A:
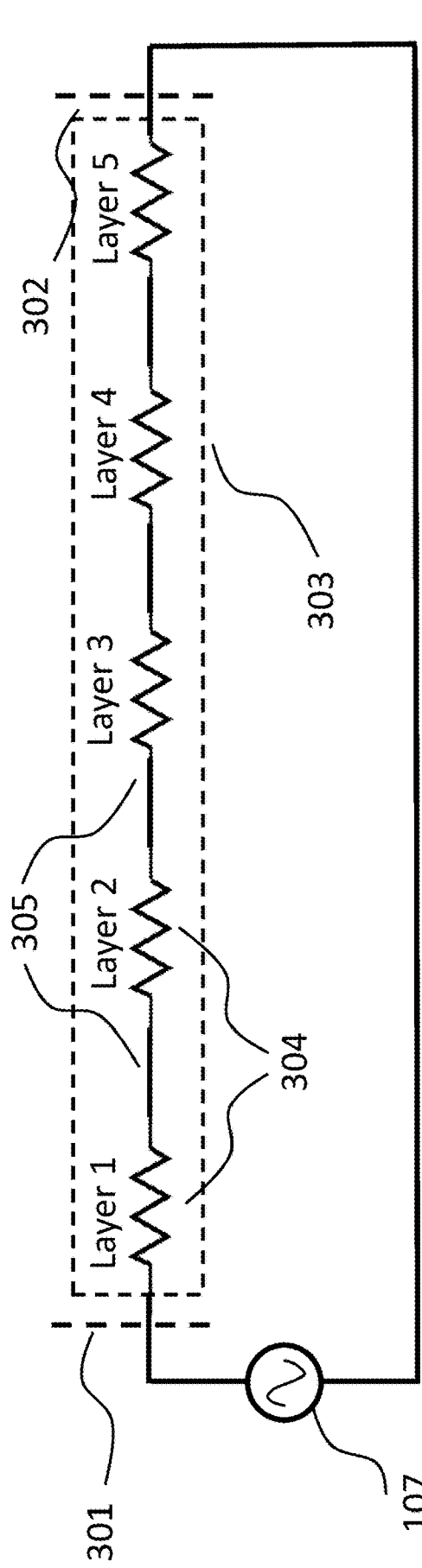
FIG. 3A is a circuit model schematic representing a system operating in a series impedance regime.

FIG. 3A shows a representative circuit model for an electromagnetic system that is subject to a series impedance regime. Device and/or apparatus boundaries 301 and 302 represent the nodes where the electromagnetic energy is incident upon the biological tissue region represented by 303. With the biological tissue 303, different layers of tissue are represented by resistances 304. The value of the resistance of each layer is dependent on the thickness of that layer of tissue and the electromagnetic properties of the layer. The representative circuit model is powered in series by an AC voltage source 107. As circuit theory dictates, the total voltage present at the nodes 305 of each layer/resistor is reduced for layers/resistors further into the biological tissue and potentially reducing the effect of the electromagnetic field in those layers. Direct electrode devices, capacitive systems/apparatuses, and other devices that substantially allow the normal component of the electric field operate primarily within a series impedance regime.

Figure 3B:
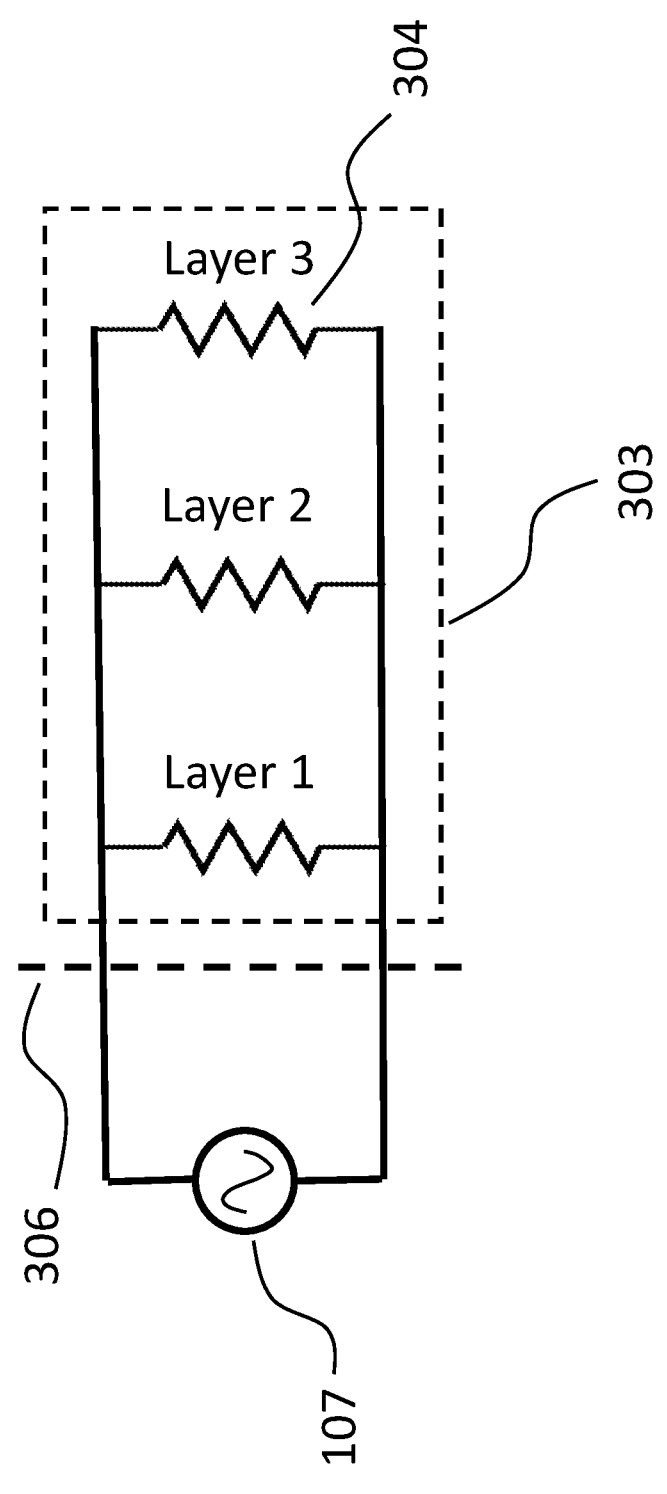
FIG. 3B is a circuit model schematic representing a system operating in a parallel impedance regime.

FIG. 3B shows a representative circuit model for an electromagnetic system that is subject to a parallel impedance regime. Device and/or apparatus boundary 306 represent the node where the electromagnetic energy is incident upon the biological tissue region represented by 303. As in FIG. 3a, different layers of tissue are represented by resistances 304 and the value of the resistance of each layer is dependent on the thickness of that layer and electromagnetic properties of the layer. The circuit is powered in parallel by an AC/RF voltage source 107. As circuit theory dictates, the total voltage present at the nodes of each layer/resistor is the same, allowing for equal application of voltage within the layers of the biological tissue 303. Antenna systems, including the apparatus introduced in this patent, and other devices that substantially allow the tangential component of the electric field operate primarily within a parallel impedance regime.

Figure 4:
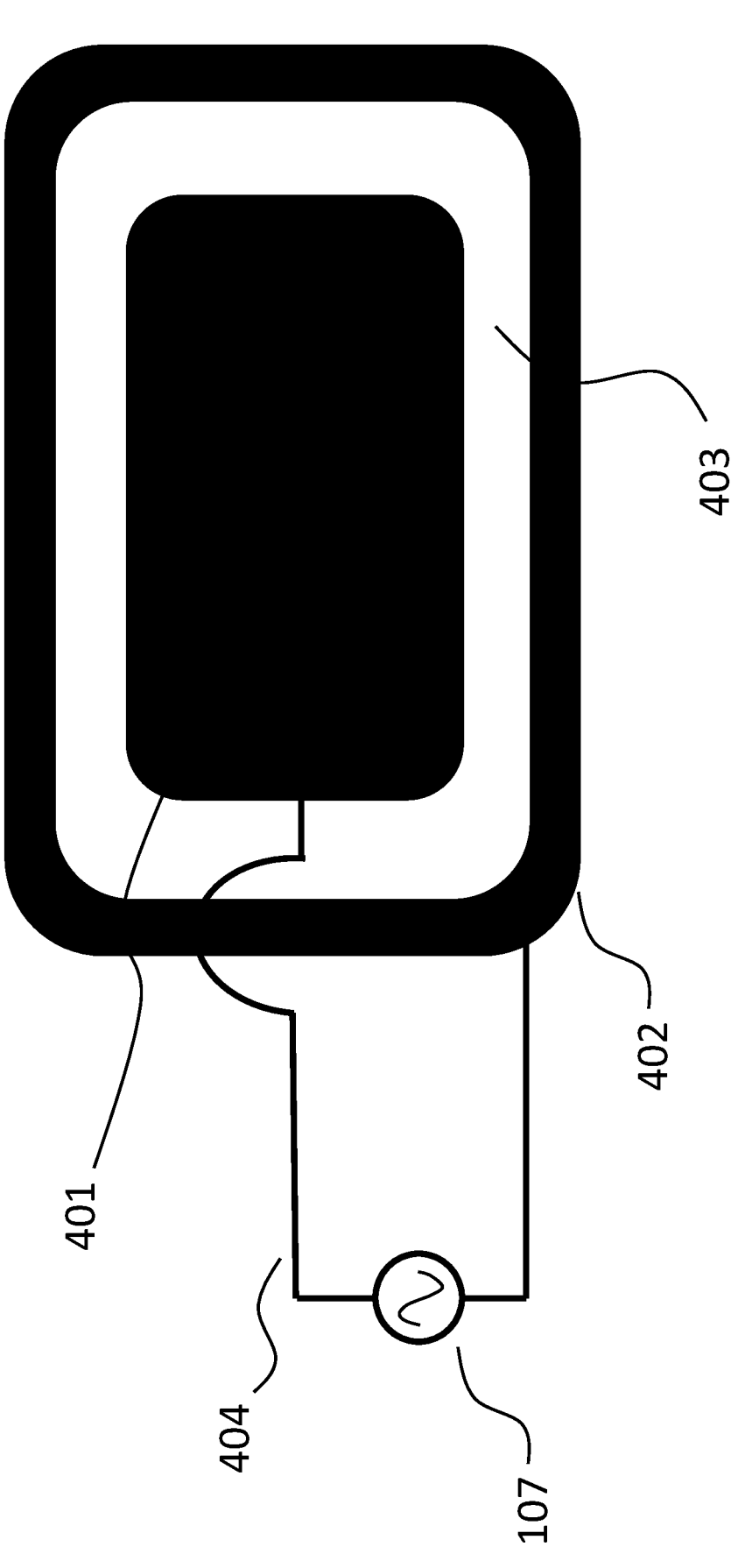
FIG. 4 is a drawing of a physical embodiment of the apparatus showing a conductive rounded rectangular disk region surrounded by a conductive ring region that is separated by a non-conductive gap.

FIG. 4 is a simple embodiment of the apparatus introduced in this invention. In this embodiment, a center rounded rectangular conductive region 401 is surrounded by a concentric rounded rectangular ring conductive region 402. The two conductive regions are separated by a non-conductive gap 403. The positive terminal of the AC voltage source 107 is attached to the central conductive region 401 and the negative terminal of the voltage source 107 is attached to the concentric conductive ring 402 by wires 404. The voltage differential that is present when wired in this configuration produces evanescent waves above and below the apparatus within the aperture of the outside conductive ring region.

Figure 5A:
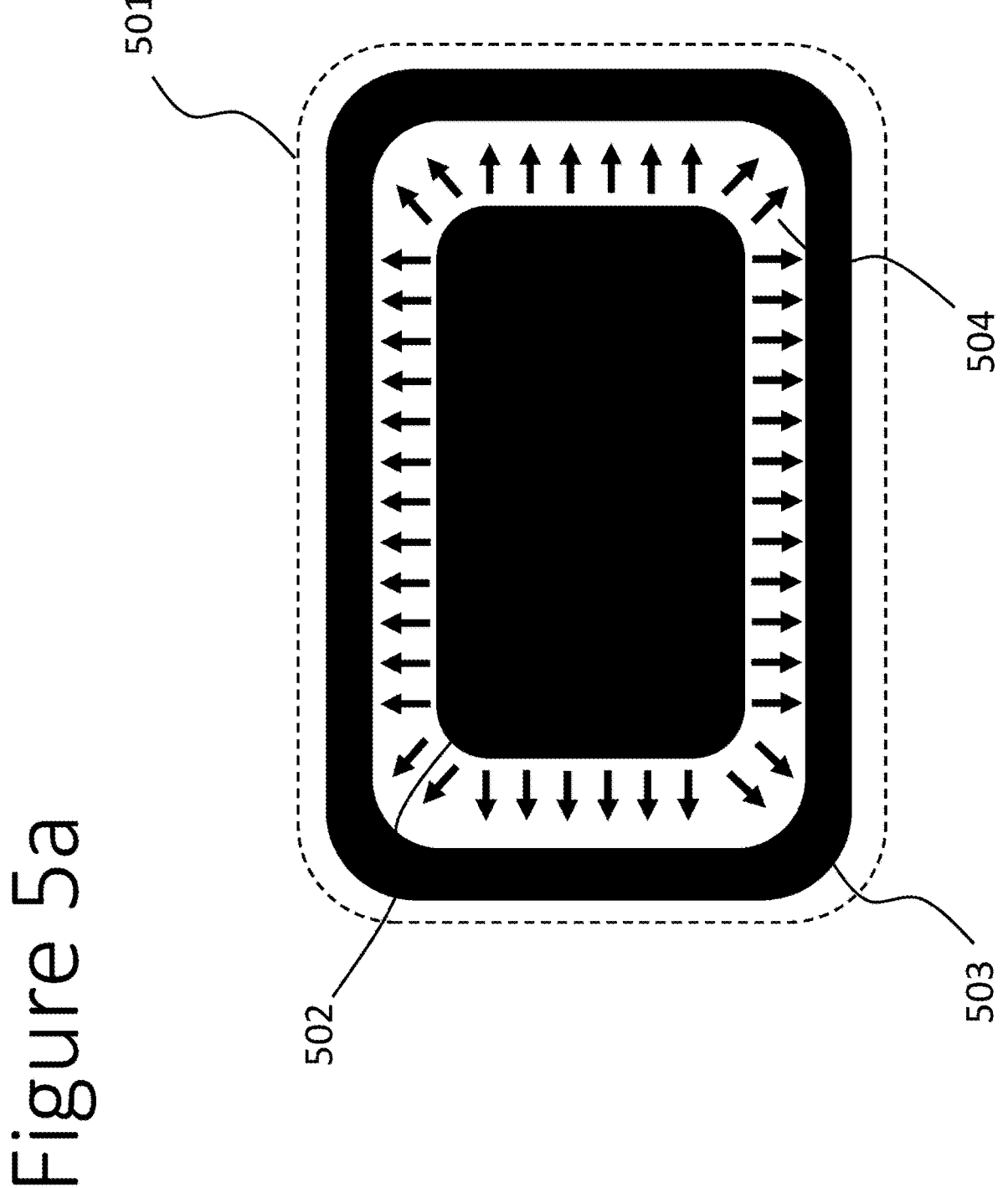
FIG. 5A is a diagram of the resultant electric field distribution of the evanescent waves for the regions adjacent to the apparatus of FIG. 4.

FIG. 5A shows the field distribution of the evanescent waves for the simple embodiment shown in FIG. 4. The apparatus 501 is comprises of a center rounded rectangular conductive region 502 surrounded by a rounded rectangular conductive region 503 separated by a non-conductive gap 504. The conductive regions are substantially insulated by non-conductive insulation material 505. When a voltage differential is applied between the center conductive region 502 and conductive region 503 the electric field polarization orients itself to point from the region with high voltage potential to the region with lower voltage potential. In the embodiment, the electric field polarization extends radially from the center conductive region 502 to the conductive region 503 as represented by the equipotential lines 506.

Figure 5B:
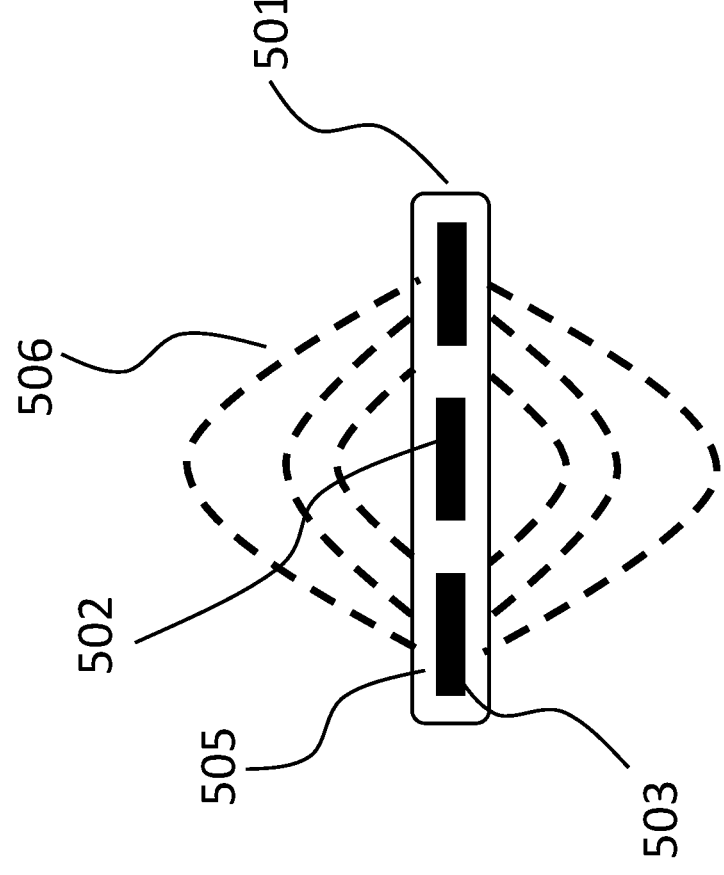
FIG. 5B is a diagram showing the side view of the apparatus in FIG. 5A and the equipotential lines.

FIG. 5B shows the spatial region where the evanescent waves extend from the planar surface of the apparatus 501 a certain distance within the aperture of the outer conductive region 503 as represented by the equipotential lines 506. The distance above and below the apparatus 501 that the evanescent waves extend is dependent of the overall voltage differential between the conductive regions 502 and 503. In particular, larger voltage differential between the regions provide for evanescent waves that extend further away from the planar aperture of the apparatus 501.

Figure 6:
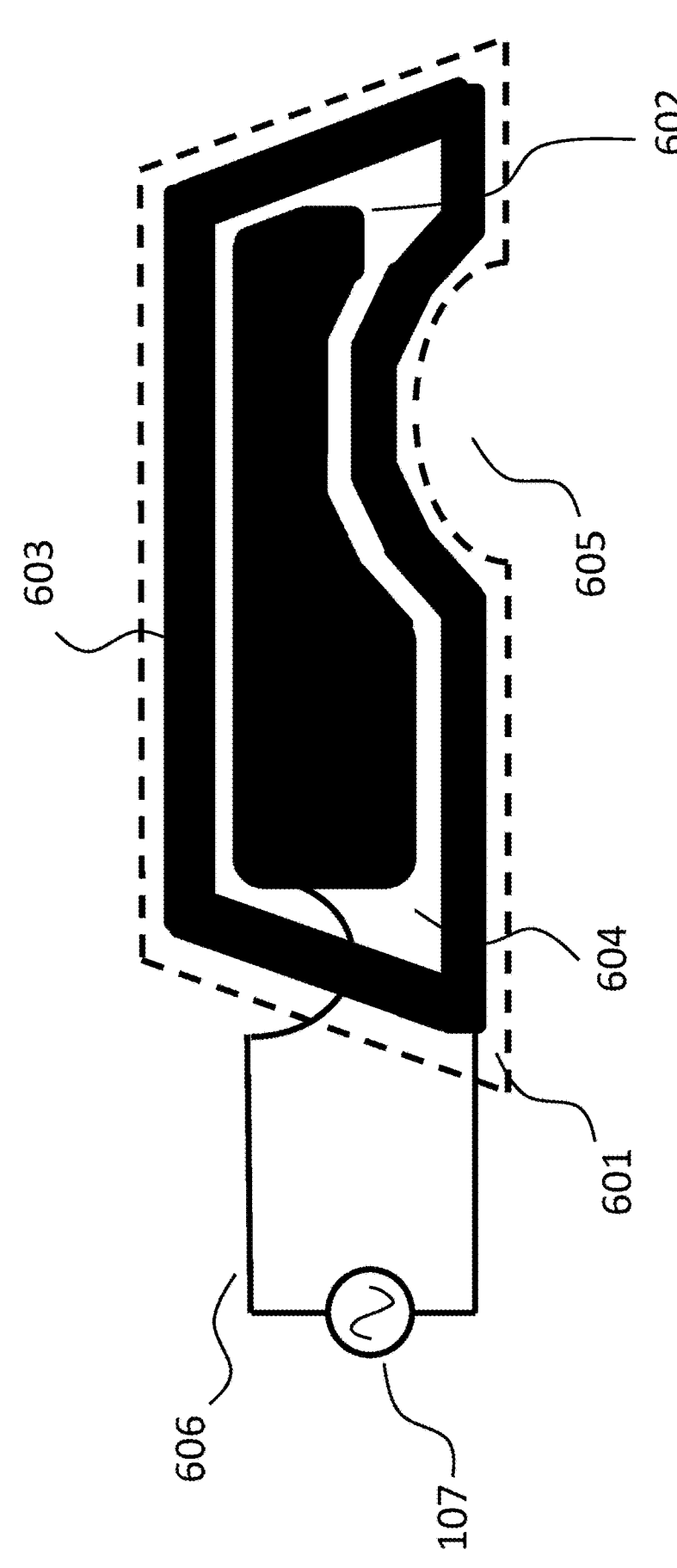
FIG. 6 is a drawing of another physical embodiment of the apparatus designed for the side of a human head.

FIG. 6 is another embodiment of the invention that is intended to be applied to the side of a human head. An apparatus 601 comprises of a central conductive region 602 surrounded outer conductive ring 603 separated by a non-conductive gap 604. The apparatus, along with the conductive regions are trapezoidal in shape to allow for conforming to the curve of the head. In addition, a cutout at the base of the apparatus 605 is present to allow for the presence of the ear on the side of the head. The apparatus is substantially insulated with non-conductive low-dielectric constant material. In this particular embodiment, a single AC voltage source 107 is connected to the apparatus by wires 606. More generally, the apparatus is not limited in shape and should be designed to fit and conform to the tissue or body part that it will be applied to. The shape of the conductive regions is not limited in shape and also can be designed to fit or conform to the object where the electromagnetic fields are being applied.

Figure 7:
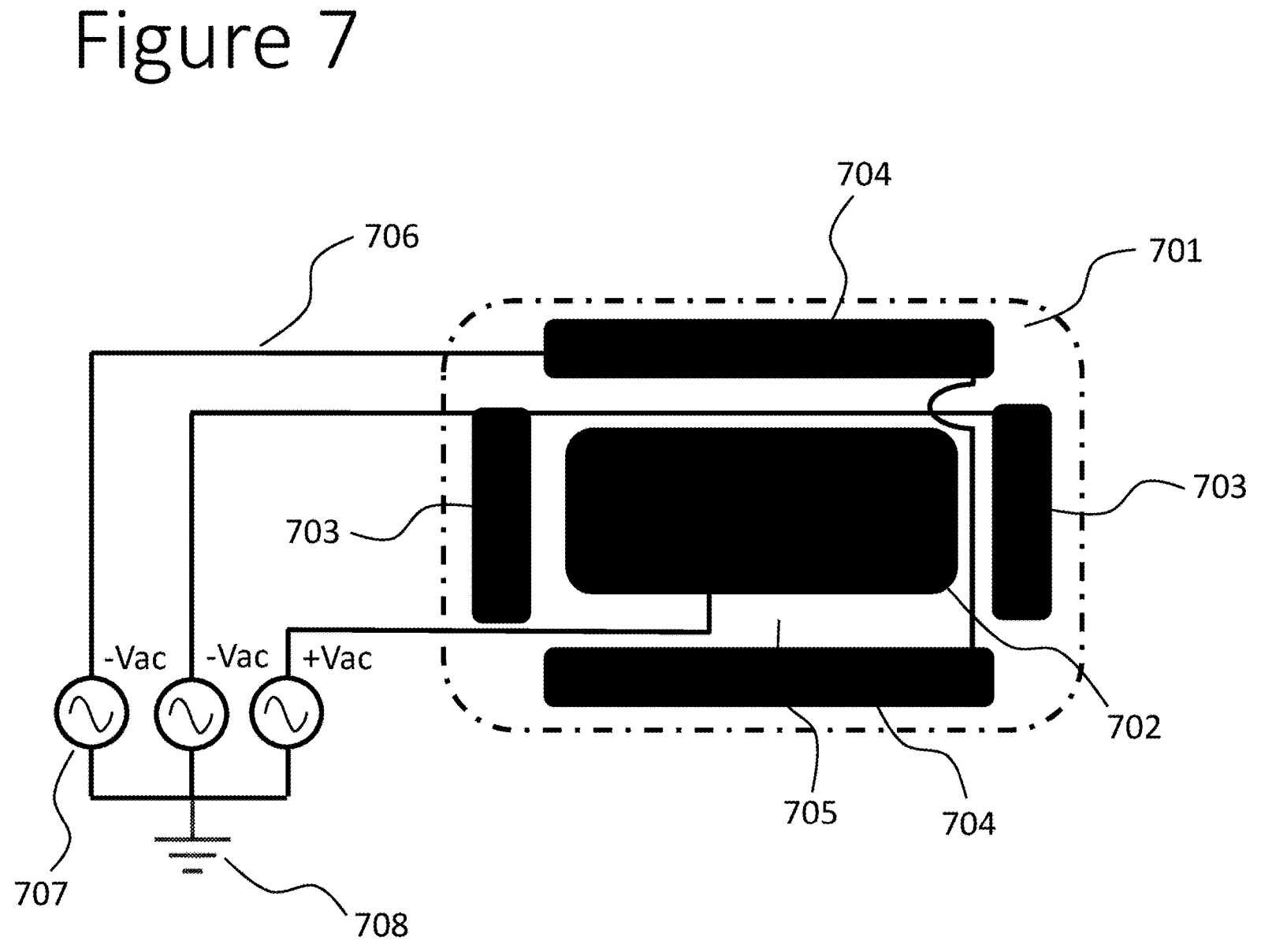

FIG. 7 is yet another embodiment of the invention that allows for dynamic polarization and field strength capabilities. An apparatus 701 comprises of a rounded rectangular central conductive region 702 with two pairs of conductive regions 703 and 704 arranged along the edge of the central conductive region 702 all separated by non-conductive gaps 705. The apparatus is substantially insulated with non-conductive low-dielectric constant material. The apparatus is powered by three separate AC/RF voltage sources 707 that are connected to the apparatus through wires 706 with one terminal of the three sources connected to ground 708. At least one source is set at an AC/RF voltage that is 180 degrees out-of-phase of the other two. When wired such that one voltage source that is 180 degrees out-of-phase is connected to the central conductive region 702 and the other two sources are connected to the other conductive regions, a voltage differential that is the sum of the voltage sources is applied to the apparatus and evanescent waves are produced.

Figure 8:
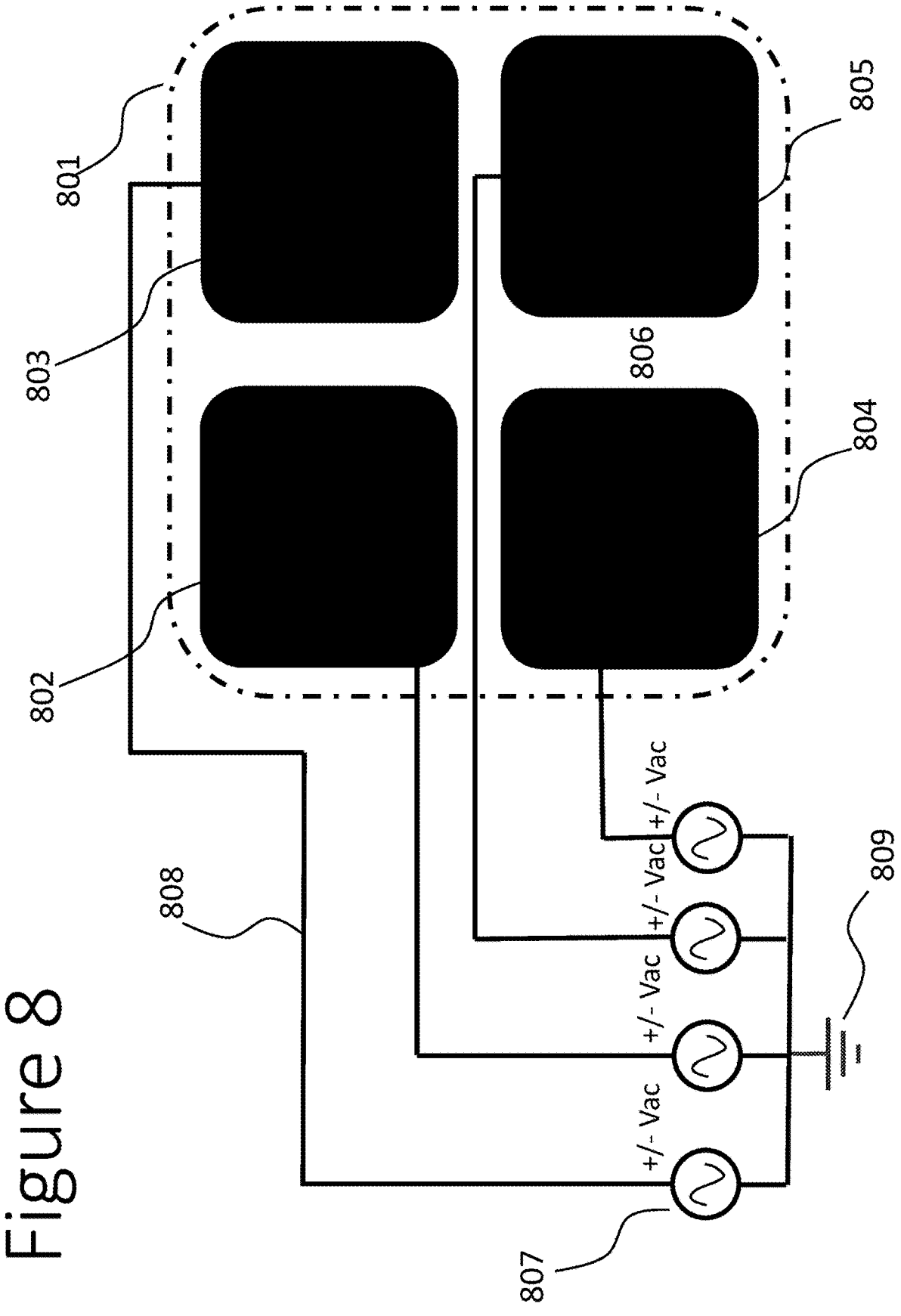
FIG. 8 is a drawing of yet another physical embodiment of the apparatus designed to provide treatment over a large volume of tissue, such as on the torso.

FIG. 8 is yet another embodiment of the invention designed to cover large volumes of biological tissue such as a torso. An apparatus 801 comprises of rounded rectangular conductive regions 802, 803, 804, and 805 placed adjacent to each other all separated by non-conductive gaps 806. The apparatus is substantially insulated with non-conductive low-dielectric constant material within the boundary of the apparatus 801. The apparatus is powered by four separate AC/RF voltage sources 807 that are connected to the apparatus through wires 808 with one terminal of the three sources connected to ground 809. Each source can be set at different voltage levels and phases to allow for dynamic and varied control of the evanescent wave. This provides different wave strengths and polarization, increasing the number of modes the apparatus can operate in.

Figure 9:
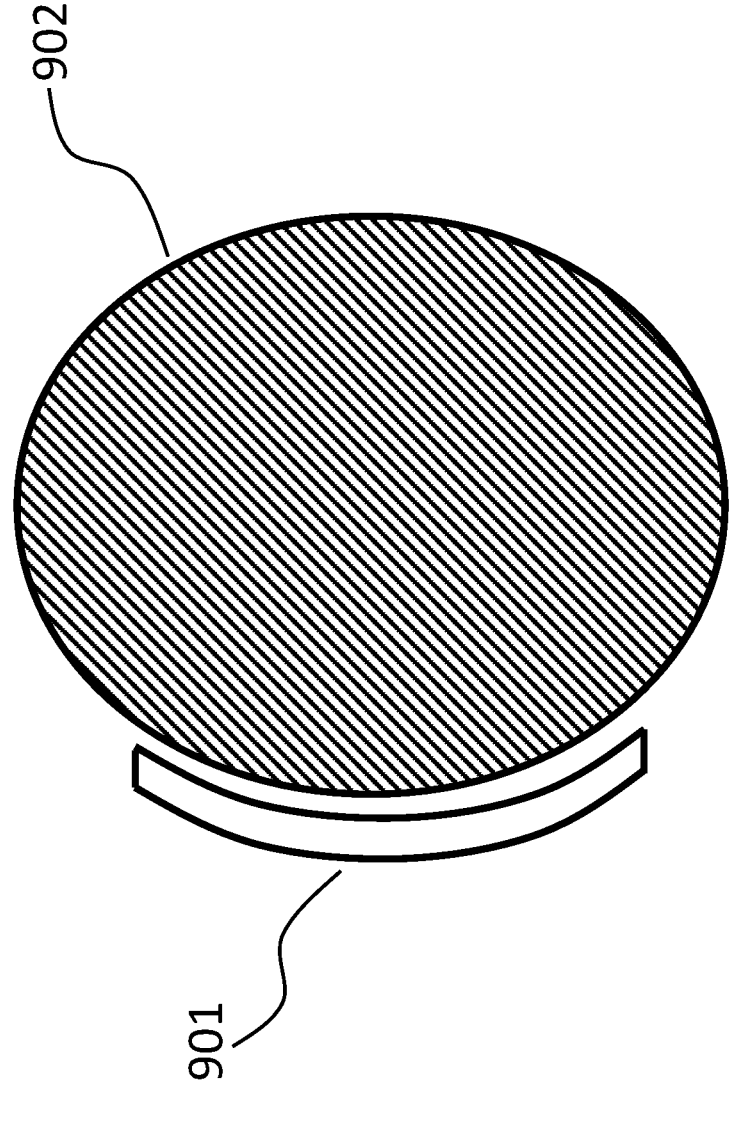
FIG. 9 is a diagram demonstrating the conformal nature of the apparatus.

FIG. 9 shows the conformal aspects of the apparatus. The apparatus 901 is designed with thin, flexible materials that can conform to the biological tissue 902. Materials of the conductive regions can be, but not limited to, copper, aluminum, silver, conductive fibers, or conductive ink. Materials of the non-conductive regions can be, but not limited to, air, plastic, polyimide, or silicone. The materials of the insulation can be, but not limited to, plastic, polyimide, Teflon, or silicone.

Figure 10:
FIG. 10 is a drawing of the apparatus conformed to the human head and treating a brain tumor.
Figure 10:
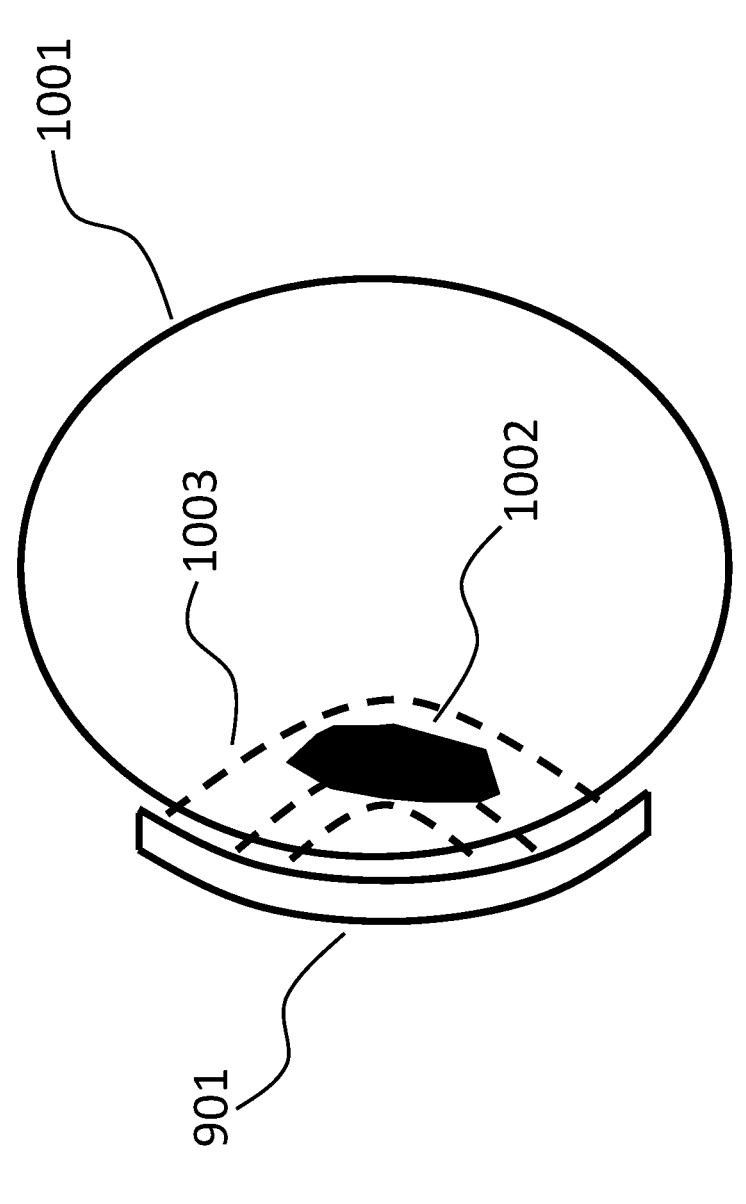

FIG. 10 shows a diagram of an application of the apparatus 901. In this application, the apparatus is attached to a human head 1001 in the vicinity of a tumor 1002. When powered the apparatus 901 produces evanescent waves (represented by equipotential lines 1003) that penetrate the head 1001 and is coupled to the tumor 1002. Other applications of this apparatus include, but are not limited to, deep brain stimulation, or therapeutic treatment.

In an example, the present invention provides an apparatus for an application of a plurality of evanescent waves to at least one biological tissue. The apparatus has an RF/voltage source generating an RF signal having a frequency of 100 kHz to 500 kHz (e.g., 150 to 300 kHz) at an output and the RF voltage sources with the ability to shift phase from 0 to 360 degrees. In an example, apparatus an electrically conducting wire(s) or RF cable(s) coupled to the output of the RF source. In an example, the apparatus has a pair of planar conductive regions configured at a voltage differential within a local region in a vicinity of a spatial volume and the configuration of the pair of planar conductive regions being spatially separated by a non-conductive gap that generates the plurality of evanescent waves within the spatial volume and the configuration reduces a formation of one or more travelling waves within the spatial volume such that a ratio of evanescent waves to travelling waves is more than ten to one and less than ten thousand to one, each of the pair of planar conductive regions comprising an overlying insulating material of a low dielectric constant material. In an example, the low dielectric material has a dielectric constant ranging from 1 to 10. The apparatus has an electric field distribution caused from the configuration of the planar conductive regions and characterizing the spatial volume, such that the spatial volume that is spatially positioned within a vicinity of a biological tissue provides a higher strength electric field than a region outside of the spatial volume such that the higher strength electric field ranges from 10 times to 105 times of a lower strength electric field in the region outside of the spatial volume.

In an example, the apparatus has other elements. In an example, the pair of planar conductive regions is configured is an evanescent wave generator. In an example, the pair of planar conductive regions is configured to deliver RF energy to the biological tissue via a plurality of reactive fields, a plurality of near field radiative waves, or a plurality of attenuating traveling waves, or any combination thereof. In an example, the pair of planar conductive regions comprises a copper, an aluminum, a conductive thread, and/or a conductive ink.

In an example, the insulating material comprises a plastic, a polyimide, a cotton, a nylon, a polyester, a polypropylene, a silk, a cellulose material, and/or a silicone. In an example, the configuration of the pair of planar conductive regions is conformal to the biological tissue. In an example, the insulating material primarily allows a tangential component of the electric field distribution to be incident upon the biological tissue and blocks a normal component of the electric field distribution from being incident upon the biological tissue.

In an example, the apparatus can be used for treating cancer tumors, deep brain stimulation, and/or other therapeutic purposes. In an example, the RF/Voltage source has a frequency range from 50 KHz to 50 MHz. In an example, more than one RF frequency is provided simultaneously or sequentially. In an example, the output of the RF source is differential, amplitude modulated, or frequency modulated, or pulse-width modulated.

In an example, the apparatus has an impedance matching network coupled between the RF voltage source and the pair of planar conductive regions to couple the RF energy efficiently to the biological tissue. In an example, the biological tissue is a solid tumor cancer. In an example, the apparatus is provided with other cancer treatments including radiation therapy, chemotherapy, immunotherapy, and surgery. In an example, the configuration of the pair of planar conductive regions are adjacent within a plane or are vertically stacked, or a first conductive region is placed within an angle of a second conductive region.

In an example, the present invention provides an apparatus for an application of a plurality of evanescent waves to at least one biological tissue. The apparatus has a plurality of RF voltage sources each of which is generating an RF signal having a frequency of 50 kHz to 50 MHz at an output and the RF voltage sources with the ability to shift phase from 0 to 360 degrees; an electrically conducting wire(s) or RF cable(s) coupled to the output of each of the RF voltage source. The apparatus has a plurality of planar conductive regions configured at a voltage differential within a local region in a vicinity of a spatial volume and the configuration of the plurality of planar conductive regions being spatially separated by a non-conductive gap that generates the plurality of evanescent waves within the spatial volume and the configuration reduces a formation of one or more travelling waves within the spatial volume such that a ratio of evanescent waves to travelling waves is more than ten to one and less than ten thousand to one, each of the plurality of planar conductive regions comprising an overlying insulating material of a low dielectric constant material, the low dielectric material having a dielectric constant ranging from 1 to 10. The apparatus has an electric field distribution caused from the configuration of the plurality of planar conductive regions and characterizing the spatial volume, such that the spatial volume that is spatially positioned within a vicinity of a biological tissue provides a higher strength electric field than a region outside of the spatial volume such that the higher strength electric field ranges from 10 times to 105 times of a lower strength electric field in the region outside of the spatial volume.

In an example, the conductive regions delivers RF energy to the biological tissue via a plurality of reactive fields, a plurality of near field radiative waves, or a plurality of attenuating traveling waves, or any combination thereof. In an example, the conductive regions comprises a copper, an aluminum, a conductive thread, and/or a conductive ink. In an example, the insulating material comprises a plastic, a polyimide, a cotton, a nylon, a polyester, a polypropylene, a silk, a cellulose material, and/or a silicone. In an example, the arrangement of the conductive region, non-conductive region, and insulation is conformal to the biological tissue. In an example, the insulation primarily allows the tangential component of the electric field to be incident upon the biological tissue and substantially blocks the normal component of the electric field from being incident upon the biological tissue.

In an example, the apparatus can be used for, but not limited to, threating solid tumors cancers, deep brain stimulation, and/or other therapeutic purposes. In an example, more than one RF voltage frequency is provided simultaneously or sequentially. In an example, the RF/Voltage sources voltage potential is provided simultaneously, sequentially, or at inverse differential between two or more conductive regions. In an example, the output of the RF voltage source is amplitude modulated, or frequency modulated, or pulse-width modulated.

In an example, the apparatus also has an impedance matching network coupled between the RF voltage source and the conductive regions element to couple the RF voltage energy efficiently to the tissue. The apparatus is provided in conjunction with other cancer treatments including, but not limited to, radiation therapy, chemotherapy, immunotherapy, and surgery. In an example, the plurality of evanescent waves are applied with other cancer treatments including radiation therapy, chemotherapy, immunotherapy, and surgery. Other applications include as a drug sensitizer and a blood-brain barrier suppressor.

Of course, one of ordinary skill in the art would recognize other variations, modifications, and alternatives.

While the above is a full description of the specific examples, various modifications, alternative constructions and equivalents may be used. Therefore, the above description and illustrations should not be taken as limiting the scope of the present invention which is defined by the appended claims.

What is claimed is:

1. An apparatus for an application of a plurality of evanescent waves to at least one biological tissue comprising;

an RF voltage source generating an RF signal having a frequency of 100 kHz to 500 kHz at an output, the RF voltage source with the ability to shift phase from 0 to 360 degrees;

an electrically conducting wire(s) or RF cable(s) coupled to the output of the RF voltage source;

a pair of planar conductive regions configured at a voltage differential within a local region in a vicinity of a spatial volume and the configuration of the pair of planar conductive regions being spatially separated by a non-conductive gap that generates the plurality of evanescent waves within the spatial volume and the configuration reduces a formation of one or more travelling waves within the spatial volume such that a ratio of evanescent waves to travelling waves is more than ten to one and less than ten thousand to one, each of the pair of planar conductive regions comprising an overlying insulating material of a low dielectric constant material, the low dielectric material having a dielectric constant ranging from 1 to 10; and an electric field distribution caused from the configuration of the planar conductive regions and characterizing the spatial volume, such that the spatial volume that is spatially positioned within a vicinity of a biological tissue provides a higher strength electric field than a region outside of the spatial volume such that the higher strength electric field ranges from 10 times to 105 times of a lower strength electric field in the region outside of the spatial volume.

2. The apparatus of claim 1 wherein the pair of planar conductive regions is configured as an evanescent wave generator.

3. The apparatus of claim 1 wherein the pair of planar conductive regions is configured to deliver RF energy to the biological tissue via a plurality of reactive fields, a plurality of near field radiative waves, or a plurality of attenuating traveling waves, or any combination thereof.

4. The apparatus in claim 1 wherein the pair of planar conductive regions comprises a copper, an aluminum, a conductive thread, and/or a conductive ink.

5. The apparatus in claim 1 wherein the insulating material comprises a plastic, a polyimide, a cotton, a nylon, a polyester, a polypropylene, a silk, a cellulose material, and/or a silicone.

6. The apparatus in claim 1 wherein the configuration of the pair of planar conductive regions is conformal to the biological tissue.

7. The apparatus in claim 1 wherein the insulating material primarily allows a tangential component of the electric field distribution to be incident upon the biological tissue and blocks a normal component of the electric field distribution from being incident upon the biological tissue.

8. The apparatus in claim 1 wherein the apparatus can be used for treating cancer tumors, deep brain stimulation, drug sensitizing, blood-brain barrier suppression, and/or other therapeutic purposes.

9. The apparatus in claim 1 wherein the RF voltage source has a frequency range from 100 kHz to 300 kHz.

10. The apparatus in claim 1 wherein more than one RF frequency is provided simultaneously or sequentially.

11. The apparatus in claim 1 wherein the output of the RF voltage source is differential, amplitude modulated, or frequency modulated, or pulse-width modulated.

12. The apparatus in claim 1 further comprising an impedance matching network coupled between the RF voltage source and the pair of planar conductive regions to couple the RF energy efficiently to the biological tissue.

13. The apparatus in claim 1 wherein the biological tissue is a solid tumor cancer.

14. The apparatus in claim 1 wherein the plurality of evanescent waves are applied with other cancer treatments including radiation therapy, chemotherapy, immunotherapy, and surgery.

15. The apparatus of claim 1 wherein the configuration of the pair of planar conductive regions are adjacent within a plane or are vertically stacked, or a first conductive region is placed within an angle of a second conductive region.

16. An apparatus for an application of a plurality of evanescent waves to at least one biological tissue comprising;

a plurality of RF voltage sources each of which is generating an RF signal having a frequency of 50 kHz to 50 MHz at an output;

each of the plurality of RF voltage sources with the ability to shift phase from 0 to 360 degrees;

an electrically conducting wire(s) or RF cable(s) coupled to the output of each of the plurality of RF voltage sources;

a plurality of planar conductive regions configured at a voltage differential within a local region in a vicinity of a spatial volume and the configuration of the plurality of planar conductive regions being spatially separated by a non-conductive gap that generates the plurality of evanescent waves within the spatial volume and the configuration reduces a formation of one or more travelling waves within the spatial volume such that a ratio of evanescent waves to travelling waves is more than ten to one and less than ten thousand to one, each of the plurality of planar conductive regions comprising an overlying insulating material of a low dielectric constant material, the low dielectric material having a dielectric constant ranging from 1 to 10; and an electric field distribution caused from the configuration of the plurality of planar conductive regions and characterizing the spatial volume, such that the spatial volume that is spatially positioned within a vicinity of a biological tissue provides a higher strength electric field than a region outside of the spatial volume such that the higher strength electric field ranges from 10 times to 105 times of a lower strength electric field in the region outside of the spatial volume.

17. The apparatus of claim 16 wherein the planar conductive regions delivers RF energy to the biological tissue via a plurality of reactive fields, a plurality of near field radiative waves, or a plurality of attenuating traveling waves, or any combination thereof.

18. The apparatus in claim 16 wherein the planar conductive regions comprises a copper, an aluminum, a conductive thread, or a conductive ink.

19. The apparatus in claim 16 wherein the insulating material comprises a plastic, a polyimide, a cotton, a nylon, a polyester, a polypropylene, a silk, a cellulose material, and/or a silicone.

20. The apparatus in claim 16 wherein the arrangement of the planar conductive regions and the insulating material are conformal to the biological tissue.

21. The apparatus in claim 16 wherein the insulating material primarily allows the tangential component of the electric field to be incident upon the biological tissue and substantially blocks the normal component of the electric field from being incident upon the biological tissue.

22. The apparatus in claim 16 wherein the apparatus can be used for, but not limited to, treating solid tumors cancers, deep brain stimulation, drug sensitizing, blood-brain barrier suppression, and/or other therapeutic purposes.

23. The apparatus in claim 16 wherein more than one RF frequency is provided simultaneously or sequentially.

24. The apparatus in claim 16 wherein the RF voltage sources voltage potential is provided simultaneously, sequentially, or at inverse differential between two or more planar conductive regions.

25. The apparatus in claim 16 wherein the output of the RF voltage source is amplitude modulated, or frequency modulated, or pulse-width modulated.

26. The apparatus in claim 16 further comprising an impedance matching network coupled between the RF voltage sources and the planar conductive regions to couple the RF energy efficiently to the tissue.

27. The apparatus in claim 16 wherein the apparatus is provided in conjunction with other cancer treatments including, but not limited to, radiation therapy, chemotherapy, immunotherapy, and surgery.

5

\*  \*  \*  \*  \*